(12) United States Patent
Philp et al.

(10) Patent No.: US 9,480,675 B2
(45) Date of Patent: Nov. 1, 2016

(54) METHOD FOR INCREASING MUSCLE GROWTH BY BLOCKING SIRTUIN ACTIVITY

(71) Applicant: THE REGENTS OF THE UNIVERSITY OF CALIFORNIA, Oakland, CA (US)

(72) Inventors: Andrew Philp, Birmingham (GB); Simon Schenk, La Jolla, CA (US); Keith Baar, Davis, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/792,388

(22) Filed: Jul. 6, 2015

(65) Prior Publication Data
US 2016/0000752 A1 Jan. 7, 2016

Related U.S. Application Data

(63) Continuation of application No. PCT/US2014/011085, filed on Jan. 10, 2014.

(60) Provisional application No. 61/751,584, filed on Jan. 11, 2013.

(51) Int. Cl.
| | | |
|---|---|---|
| *A01N 43/16* | (2006.01) | |
| *A61K 31/366* | (2006.01) | |
| *A61K 31/166* | (2006.01) | |
| *A61K 31/185* | (2006.01) | |
| *A61K 31/353* | (2006.01) | |
| *A61K 45/06* | (2006.01) | |

(52) U.S. Cl.
CPC .......... *A61K 31/366* (2013.01); *A61K 31/166* (2013.01); *A61K 31/185* (2013.01); *A61K 31/353* (2013.01); *A61K 45/06* (2013.01)

(58) Field of Classification Search
CPC .................................................. A61K 31/366
USPC ........................................................ 514/455
See application file for complete search history.

(56) References Cited

U.S. PATENT DOCUMENTS

| | | | | |
|---|---|---|---|---|
| 7,291,699 | B2* | 11/2007 | Brodsky ............ | C07K 14/4707 435/325 |
| 2005/0287597 | A1* | 12/2005 | Ott .......................... | C12Q 1/26 435/7.1 |

OTHER PUBLICATIONS

Philip et al., Journal of Biological Chemistry. Jul. 11, 2011, vol. 286; pp. 30561-30570.*
Sun et al. The Journal of Nutrition, 1986, 116, 2409-2414.*
United States Patent and Trademark Office (USPTO), international search report and written opinion, PCT/US2014/011085, issued Apr. 8, 2014, pp. 1-10, with claims searched, pp. 11-13, counterpart to U.S. Appl. No. 14/792,388.
Philp, A et al. Sirtuin 1 (SIRT1) Deacetylase Activity Is Not Required for Mitochondrial Biogenesis or Peroxisome Proliferator-Activated Receptor-Gamma Coactivator-1-Alpha (PGC-1-Alpha) Deactylation Following Endurance Exercise. Journal of Biological Chemistry. Jul. 11, 2011, vol. 286; pp. 30561-30570.
Sun, S et al. Muscle Creatine Content in Rats Given Repeated Large Doses of Nicotinamide: Effects of Dietary Methionine, Choline, Carnitine, and Other Supplements. Journal of Nutrition. Dec. 1, 1986, vol. 116; pp. 2409-2414.

\* cited by examiner

*Primary Examiner* — Nizal Chandrakumar
(74) *Attorney, Agent, or Firm* — O'Banion & Ritchey LLP; John P. O'Banion

(57) ABSTRACT

Systems and methods are described providing therapeutic preparations of sirtuin inhibitors, such as SIRT1 inhibitors, for stimulating load-induced skeletal muscle growth in the body of a patient. The natural stimulation of SIRT1 activity can be suppressed through increased caloric intake and loading in conjunction with the inhibition of sirtuin activity to improve the inhibitory effect. In addition, known muscle growth promoting agents such as amino acids and hormones can be administered at the same time as the sirtuin inhibitor. The size of the tissue structure to be treated or the body size may be used to determine the therapeutic dose of sirtuin inhibitor. The sirtuin inhibitor and muscle stimulating agents are either locally or systemically delivered at therapeutic doses for the desired effect. The SIRT1 inhibitor Splitomycin is particularly effective.

17 Claims, 7 Drawing Sheets

METHOD FOR INCREASING MUSCLE GROWTH BY BLOCKING SIRTUIN ACTIVITY

CROSS-REFERENCE TO RELATED APPLICATIONS

This application is a 35 U.S.C. §111(a) continuation of PCT international application number PCT/US2014/011085 filed on Jan. 10, 2014, incorporated herein by reference in its entirety, which claims priority to, and the benefit of, U.S. provisional patent application Ser. No. 61/751,584 filed on Jan. 11, 2013, incorporated herein by reference in its entirety. Priority is claimed to each of the foregoing applications.

The above-referenced PCT international application was published as PCT International Publication No. WO 2014/110399 on July 17, 2014, which publication is incorporated herein by reference in its entirety.

STATEMENT REGARDING FEDERALLY SPONSORED RESEARCH OR DEVELOPMENT

This invention was made with Government support under AG043120, AR058878, RR024146, and TR000002, awarded by the National Institutes of Health. The Government has certain rights in the invention.

INCORPORATION-BY-REFERENCE OF MATERIAL SUBMITTED IN A COMPUTER PROGRAM APPENDIX

Not Applicable

BACKGROUND OF THE INVENTION

1. Field of the Invention

This invention pertains generally to load-induced muscle growth and strength training and more particularly to methods for improving muscle hypertrophy in mammals by inhibiting sirtuins in muscles in combination with other muscle growth approaches.

2. Description of Related Art

Skeletal muscle is a very adaptive tissue and muscle mass in the body is regulated by nutritional, hormonal and mechanical cues. Muscular strength is directly linked to health, such that the mortality rate of individuals with low muscle strength is twice that of a high strength counterpart. Functionally, low muscle strength limits mobility, independence, and recovery from surgery and metabolically low muscle mass increases the risk of diseases such as diabetes. Therefore, increasing muscle mass and strength has important implications on the health, longevity, and quality of life of people.

Generally, muscle hypertrophy, or the enlargement of muscle fibers, is a process that includes load-induced changes in transcription and translation in the cells through a number of pathways. For example, the IGF-1 signaling pathway is a well-known cascade contributing to the development of skeletal muscle hypertrophy.

Increased activity of the mechanistic target of rapamycin (mTOR) correlates with and is required for skeletal muscle growth. Factors associated with reduced cellular energy status have been proposed to suppress mTOR signaling and thereby limit skeletal muscle hypertrophy. However, whether this effect is mediated exclusively by the metabolic stress proteins described to date has yet to be demonstrated.

The $NAD^+$-dependent protein deacetylase, sirtuin1 (SIRT1), is another candidate for integrating and transducing changes in cellular energy flux to the muscle and preventing growth. SIRT1 activity is increased by metabolic stress such as seen during calorie restriction or endurance exercise. Both caloric restriction and endurance exercise are known to blunt muscle growth, suggesting that SIRT1 might inhibit muscle protein synthesis and the hypertrophic response to loading.

Accordingly, there is need for preparations and methods that will help reverse age related muscle atrophy or allow for accelerated skeletal muscle growth from weight training. The present invention satisfies these needs as well as others and is an improvement in the art.

BRIEF SUMMARY OF THE INVENTION

The present invention provides a method of increasing the amount of skeletal muscle growth in mammals following a growth stimulus using any sirtuin inhibitor. It has been shown that in the absence of the sirtuin SIRT1, muscle grows twice as much as when SIRT1 is present. Therefore, inhibiting SIRTs can lead to an increase in load-induced muscle hypertrophy. The process can be augmented with amino acid and protein supplements and nutrition.

Protein acetylation has been shown to be part of regulation in a wide array of cellular pathways, including those related to growth such as the activity of the growth related p70 S6 kinase (S6K). To demonstrate the role of SIRT1 in modulating skeletal muscle growth, in vivo, the gastrocnemius and soleus muscles were removed in mice and the rate of compensatory growth in the plantaris (PLN) was determined.

Using SIRT1 knockout mice (mKO), it was shown that increasing the load across a muscle for 2 weeks resulted in a $137\pm18.1\%$ increase in muscle mass, whereas in the control mice the increase in muscle mass was $64\pm8.2\%$ over the same time period. In mOX mice with muscle-specific over expression (OX) of SIRT1, adaptive growth was moderately reduced compared to the control FLX mice (~25% lower than FLX).

Since SIRT1 can be inhibited with drugs and nutrients, this is a strategy that can be used to increase muscle mass and strength. For example, 14 days of daily injection of the SIRT1 inhibitor Splitomycin increased muscle hypertrophy 65% more than vehicle injection without affecting basal muscle mass. Interestingly, manipulation of SIRT1 did not affect the phosphorylation status of key proteins in the mTOR signaling cascade (S6K1, 4E-BP1, AKT, TSC2), which have previously been reported to be required for skeletal muscle growth.

In one embodiment, a method for increasing skeletal muscle growth in mammals is provided comprising inhibiting the activity of sirtuins in skeletal muscles and loading the skeletal muscles that have inhibited sirtuins activity.

In another embodiment, a method for increasing skeletal muscle growth in mammals, is provided that inhibits the activity of SIRT1 in skeletal muscles of a mammal by delivering an inhibitor and the natural stimulation of SIRT1 is suppressed in the mammal. Loading of the skeletal muscles that has inhibited SIRT1 activity produces greater muscle growth. The natural stimulation of SIRT1 activity can be avoided by increasing calorie intake of the mammal and by loading the skeletal muscles of the mammal without aerobic activity.

According to another embodiment of the invention, a therapeutic dose of a SIRT1 inhibitor is delivered to skeletal muscles of a mammal by injection. The preferred therapeutic dose of SIRT1 inhibitor is between about 0.25 to about 50 mg/kg body weight of the mammal. A preferred SIRT1 inhibitor is Splitomycin delivered by a therapeutic dose of 25 mg/kg body weight. Other SIRT1 inhibitors, such as the indoles, the natural product inhibitors identified by Holzhauser et al (Angew. Chem. Int. Ed. 52:5171; 2013), and as yet to be identified molecules that inhibit SIRT1 at an appropriate therapeutic dose would be included.

According to a separate embodiment of the invention, a therapeutic dose of a SIRT1 inhibitor is delivered to persons recovering from bed rest, injury, immobilization or space flight. The administration of a therapeutic dose of SIRT1 inhibitor to individuals undergoing therapy to recover from any of these conditions should accelerate the rate of muscle repair and recovery.

According to a separate embodiment of the invention, a therapeutic dose of a SIRT1 inhibitor is delivered to aging persons who are unable to maintain muscle mass due to sarcopenia. The administration of a therapeutic dose of SIRT1 inhibitor to individuals suffering from sarcopenia, together with rehabilitative exercises should accelerate the rate of muscle growth in these individuals.

According to a separate embodiment of the invention, a therapeutic dose of a SIRT1 inhibitor is delivered to aging persons who are unable to maintain muscle mass due to cachexia (the loss of muscle due to cancer/burn/kidney disease). The administration of a therapeutic dose of SIRT1 inhibitor to individuals suffering from cachexia, together with rehabilitative exercises should accelerate the rate of muscle growth in these individuals.

In a separate embodiment of the invention, a therapeutic dose of a SIRT1 inhibitor is delivered to developing livestock to increase the rate of growth of animals and decrease the time to slaughter.

Other agents that increase muscle hypertrophy such as amino acids work in a different way and therefore these interventions are additive. Therefore, in one embodiment, amino acid administrations used in conjunction SIRT1 inhibition for the stimulation of muscle growth.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Figure 1:
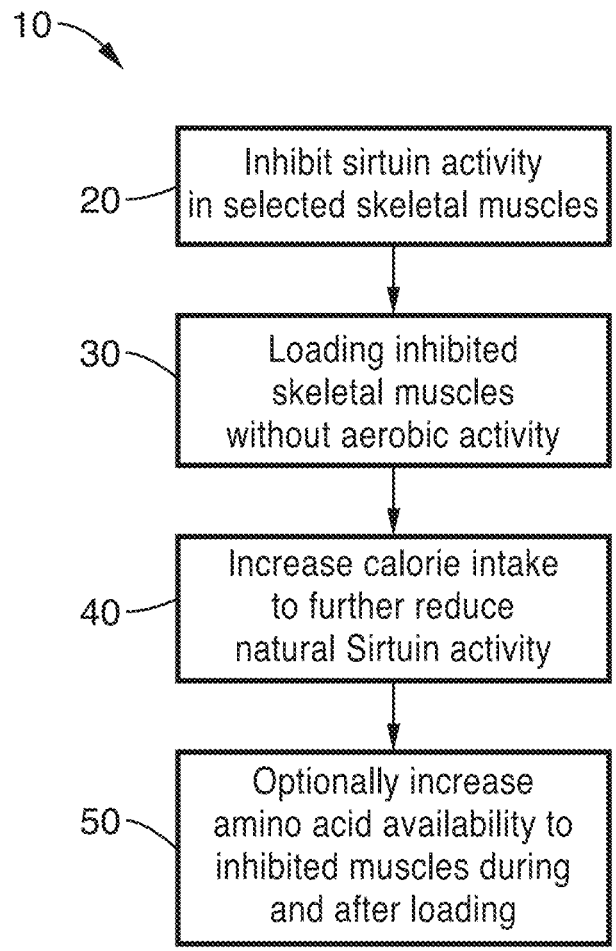
FIG. 1 is a flow diagram of one method for inducing skeletal muscle growth using a sirtuin inhibitor according to the invention.

Referring more specifically to the drawings, for illustrative purposes one embodiment of the methods for inducing skeletal muscle growth of the present invention is described and depicted generally in FIG. 1. It will be appreciated that the methods may vary as to the specific steps and sequence without departing from the basic concepts as disclosed herein. The method steps are merely exemplary of the order that these steps may occur. The steps may occur in any order that is desired, such that it still performs the goals of the claimed invention.

Turning now to FIG. 1, a flow diagram of one embodiment of a method 10 for inducing skeletal muscle growth is shown. In the step at block 20, the activity of one or more Sirtuins is substantially inhibited in selected skeletal muscles. The Sirtuins are a family of $NAD^+$-dependent protein deacetylases and ADP-ribosyltransferases that are important regulators of cellular metabolism, stress response, cell differentiation and senescence.

One sirtuin for inhibition is sirtuin 1 (SIRT1), with activity that can be inhibited by a number of approaches including the introduction of particular pharmaceutical preparations as well as certain physiological conditions such as increased caloric intake. Such approaches for inhibiting the activity of SIRT1, for example, may be cumulative and have different effective durations.

One particularly desirable pharmaceutical preparation for inhibiting SIRT1 activity is Splitomycin. Although Splitomycin is a preferred inhibitor, other SIRT1 inhibitors such as Suramin Sodium, Salermide, EX 527, Tenovin-6, SIRT1 Inhibitor IV-(S)-35, SIRT1/2 Inhibitor IV-Cambinol, SIRT2 Inhibitor-AGK2, Sirtinol and Tenovin-1 can be used alone or in combination. Other inhibitory preparations include nicotinamide, indoles, and natural product inhibitors.

The sirtuin inhibitors may be isolated and purified from natural sources or from bioengineered sources, or may be synthesized, and may be combined into, with, or on a temporary implant for local elution or otherwise as a liquid or powder to be mixed in a carrier vehicle for injection delivery. The sirtuin inhibitors may be either locally or systemically delivered at therapeutic doses for the desired effect.

Inhibition, when used with respect to sirtuin or SIRT1 activity, indicates that the deacetylase and ADP-ribosyl-transferase or other measurable activity of the sirtuin is reduced to a detectable level from that which is normally occurring. However, significant inhibition of sirtuin activity is preferred ranging from more than 10% below the maximum detectable activity level to approximately 90% below the maximum detectable activity level.

Inhibition of selected skeletal muscle sirtuins is preferably achieved with an oral administration or injection of a sirtuin inhibitor. An injection or exercise (which shifts blood flow and therefore increases the delivery of the compound to the appropriate muscles) around the time of administration of the inhibitor is preferred so that specific muscles or muscle groups can be targeted for treatment. However, other delivery modalities can be employed to produce the inhibitory effect.

A pharmaceutically acceptable inhibitor is selected and an effective amount is prepared in solution with an appropriate carrier vehicle for injection or other delivery modality. A pharmaceutically acceptable formulation refers to materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The inhibitor may be either injected directly into the tissue structure to be treated, taken orally, or delivered with an implant for elution delivery, depending upon the particular therapy to be employed.

It will be appreciated according to certain further embodiments that therapeutic preparations of sirtuin activity inhibitor and related methods include identifying, and in some cases preparing, a particular therapeutic dose to meet a particular condition in the muscle tissue, typically based upon size (e.g. volume or area) of tissue to be treated. For example, a particular dose is identified in relation to the size of the individual to be treated.

An effective amount of an inhibitory composition or compound refers to a nontoxic but sufficient amount of the composition or compound to provide the desired result. The exact amount required may vary from subject to subject, depending on the species, age, and general condition of the subject, the particular composition or compound used, its mode of administration, and other routine variables. An appropriate effective amount can be determined by one of ordinary skill in the art using only routine experimentation.

It is also to be appreciated that the terms "dose" or "dosing" are herein intended to include both a definition related to quantity, concentration, volume, and/or rate of delivery in the acute administration setting, as well as a temporal definition that includes frequency and duration of a multiple treatment protocol to provide an overall therapeutic effect.

After the sirtuin activity in selected skeletal muscles has been inhibited at block 20, the inhibited muscles are subject to loading, preferably to failure. The time frame for loading of inhibited muscles begins approximately with the delivery of inhibitor and preferably extends through the time that the muscle is no longer inhibited. Loading of the muscles can be continuous or episodic. However, loading of inhibited muscles preferably occurs at least through the half-life of the inhibitor in the muscle or muscle groups that have been selected.

Loading of skeletal muscles at block 30 can occur through conventional weight training or resistance training exercises. Any loading parameters used will be effective in increasing muscle mass in association with SIRT1 inhibition provided that a sufficient load is delivered to the muscle. Sufficient load must be determined on an individual basis.

Natural SIRT1 activity can also be diminished by an increase in calorie intake. Accordingly, at block 40 of FIG. 1, the patient can increase the calorie intake prior to and after the delivery of the inhibitor at block 20 and loading at block 30 in one embodiment. It can be seen that concurrent approaches of SIRT1 inhibition at block 20 and block 40 allows some temporal control over SIRT1 levels in selected skeletal muscles and the duration and maximization of the effects of loading of the muscles at block 30.

The beneficial effect of loading of the skeletal muscles that have inhibited SIRT1 activity to produce muscle growth can be accentuated with other known muscle hypertrophy stimulating materials such as amino acids and hormones. Accordingly, at block 50 of FIG. 1, the method uses sirtuin inhibition in conjunction with the administration of amino acids such as those found in whey protein or any protein source with a readily absorbed amount of the amino acid leucine, for example. In one embodiment, muscle growth supportive nutritional supplements, and diets are used in parallel to maximize the effect of loading inhibited skeletal muscles.

The duration of each step in the treatment shown in FIG. 1 as well as the duration of the overall course of treatment can be selected to achieve the desired results. For example, the course of treatment may be a single therapeutic dose of a sirtuin inhibitor or the course of treatment may also be more than one day with a therapeutic dose or doses of inhibitor administered daily.

The SIRT1 inhibitor, Splitomycin delivered by a therapeutic dose of 25 mg/kg body weight per day has been shown to be effective. The effective dose of other SIRT1 inhibitors such as the indoles, and the natural product inhibitors described above can be determined on a case by case basis.

A therapeutic dose may also include a muscle growth promoting agent such as amino acids or hormones delivered simultaneously with the sirtuin inhibitor or combination of inhibitors.

In another embodiment, the duration comprises at least about a two week period and the therapeutic dose between about 0.025 mg to about 50 mg/kg body weight being delivered per day over the duration of the treatment.

The invention may be better understood with reference to the accompanying examples, which are intended for purposes of illustration only and should not be construed as in any sense limiting the scope of the present invention as defined in the claims appended hereto.

EXAMPLE 1

In order demonstrate the role of SIRT1 in modulating skeletal muscle growth, compensatory growth studies were conducted in two SIRT1 mouse models: mice with muscle-specific knockout of SIRT1 deacetylase activity (mKO) and muscle-specific over expression (mOX) of SIRT1 and floxed (WT) control mice. The rate of compensatory growth (CG) in the plantaris (PLN) was determined by surgically removing the gastrocnemius and soleus muscles and evaluating (CG) growth over time.

Generation of the SIRT1 mKO mice uses floxed mice harboring loxP sites flanking exon 4 of the SIRT1 gene (SIRT1 FLX-exon4), which encodes the deacetylase domain of SIRT1. These mice were crossed with mice expressing Cre recombinase under the control of the muscle creatine kinase promoter (MCK-Cre). In these mice, a truncated SIRT1 protein is present, but the protein lacks deacetylase activity.

The SIRT1 mOX mice were generated using mice with a transcriptional stop cassette (STOP) flanked by loxP sites upstream of the SIRT1 cDNA that were crossed with MCK-Cre mice. After Cre-mediated recombination, the STOP cassette is removed and SIRT1 gene expression is driven by a constitutive promoter (CAGGS) thereby generating mice with muscle-specific overexpression of SIRT1. For simplicity, the foxed mice used to generate mKO and mOX mice are referred to as wild type (WT) mice. Mice were housed on a 12:12 hour light:dark cycle, and only male mice were used.

The plantaris (PLN) muscle in test subjects was overloaded by removal of the gastrocnemius (GTN) and soleus (SOL) muscles, termed synergist ablation. Briefly, test animals were anaesthetized and the area above the incision shaved and sterilized. The SOL and GTN were isolated and severed at the Achilles tendon. The complete SOL and the distal two thirds of the GTN were removed leaving the PLN muscle and their blood and nerve supply intact. The overlying skin was sutured with 6-0 vicryl and the animal was then given the analgesic and moved to a temperature-controlled environment to recover. All animals returned to normal activity within one hour. Animals were monitored on a daily basis for signs of pain or post-operative infection. No signs of discomfort or distress were noted throughout the 6-14 days of overload. On the day of collection, animals were anaesthetized and overloaded and contralateral control muscles were rapidly removed, rinsed in PBS, all connective/scar tissue was removed using a dissection microscope, then the muscles were snap frozen in liquid nitrogen, and stored at −80° C. until processed.

The generation and care of the SIRT1 mOX and mKO mice was approved by and were conducted in accordance with the Animal Care Program at the University of California, San Diego. Surgical and collection procedures on all animals took place under inhaled anesthetic using a 2.5% concentration of isoflurane. Animals were treated with analgesics (Buprenex 0.05 mg/kg) and allowed to recover in a warm environment. The animals were euthanized after muscle collection under anesthesia.

After collection, muscle samples were prepared for Western Blot analysis by being powdered on dry ice using a mortar and pestle and then homogenized in 10-fold mass excess of ice cold sucrose lysis buffer (50 mM Tris pH 7.5, 250 mM Sucrose, 1 mM EDTA, 1 mM EGTA, 1% Triton X 100, 50 mM NaF, 1 mM $NaVO_4$ $Na_2(PO_4)_2$ and 0.01% DTT). The homogenate was vortexed for 30 minutes at 4° C. and centrifuged for 10 minutes at 10,000×g and 4° C. to remove insoluble material. Protein concentrations were determined using the DC protein assay (Bio-Rad, Hercules; California, USA). Equal aliquots of protein were diluted in Laemmli sample buffer and boiled for 5 mins. 10-25 µg of sample was then subjected to SDS-PAGE on 10-15% acrylamide gels at a constant current of 58 mA and transferred to Protran nitrocellulose membrane (Whatman; Dassel, Germany) using a BioRad semidry transfer apparatus at 100V for 1 hour. Membranes were blocked in 5% dry milk in TBS-T and then incubated over night at 4° C. with appropriate primary antibody in TBST at 1:1000. The membranes were then washed 3× in TBST before incubation for 1 hour at room temperature with peroxidase-conjugated secondary antibodies in TBST at 1:10000 (Perbio Science; Cramlington, UK). Antibody binding was detected using an enhanced chemiluminescence HRP substrate detection kit (Millipore; Watford, UK). Imaging and band quantification were carried out using a Chemi Genius Bioimaging Gel Doc System (Syngene; Cambridge, UK).

Lysine acetylation immunoprecipitation (IP) analysis was performed on extracts from control and ABL plantaris muscle samples prepared above for Western Blot. For acetylation measurements of S6K1 and p53, nuclear fractions were isolated in the presence of 1 µM trichostatin A and 10 mM nicotinamide. 500 µg homogenates were rotated overnight at 4° C. with the appropriate primary antibody. Rabbit anti-S6K1 was obtained from Santa Cruz Biotechnology (California, USA), rabbit-anti: p-S6K1$^{T389}$, p-PKB$^{T308}$, t-PKB, were obtained from Cell Signaling Technologies (Massachusetts, USA). The following day, 25 µl of protein A sepharose beads were added to the homogenate/antibody mix and rotated for an additional 2 hours. Following which, beads were washed six times before the protein was eluted in 1×LSB at 100° C. for 5 minutes.

To determine whether SIRT1 was activated by overload, the GTN and SOL muscles of rats were surgically removed and the activity of SIRT1 was monitored by determining the acetylation of its target p53. An increase in muscle mass (% of contralateral control) of rat plantaris (PLN) muscle was seen during 6 and 9 days after synergist ablation. This growth phase occurs concurrently with phosphorylation and acetylation of S6K1.

Figure 2A:
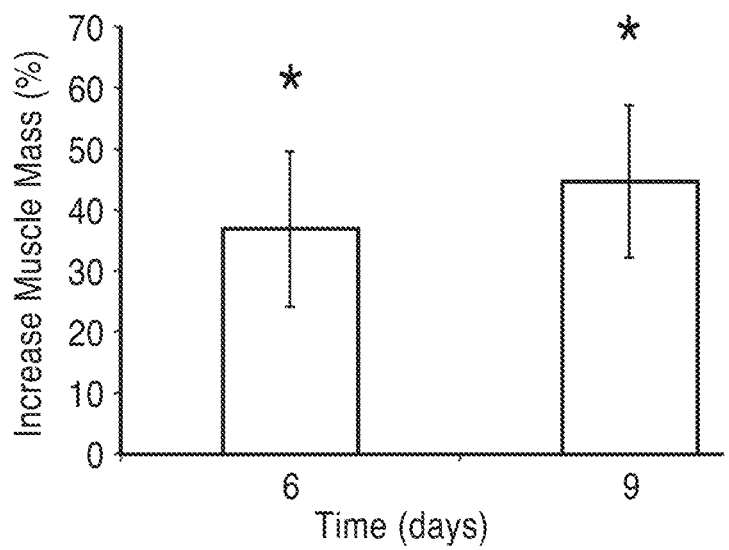
FIG. 2A is a graph showing an increase in muscle mass of a rat plantaris muscle at 6 and 9 days synergist ablation.
Figure 2B:
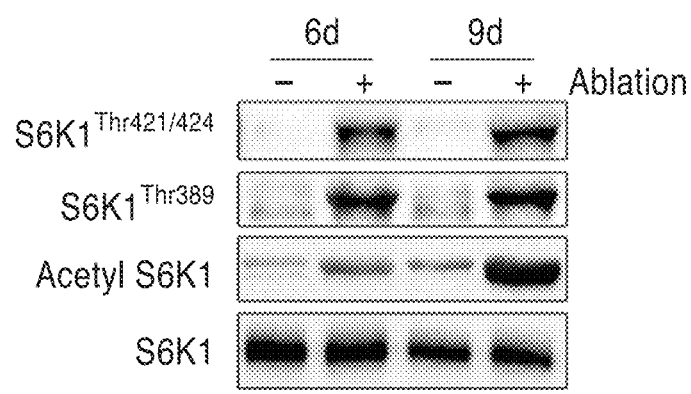
FIG. 2B is a blot assay result for S6K1 acetylation at day 6 and day 9 in response to chronic growth.
Figure 2C:
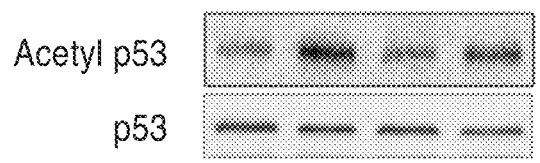
FIG. 2C is a blot assay result for p53 acetylation at day 6 and day 9 in response to chronic growth.

As seen in FIG. 2B and FIG. 2C, increased S6K1 and p53 acetylation occurs in response to chronic growth in vivo. S6K1 acetylation increased at day 3 (vs. the contralateral control), and remained high at 6, 9, 12 and 21 days. At the same time, an increase in S6K1 phosphorylation and a reduction in SIRT1 activity, as measured by increased p53 acetylation, was observed.

Accordingly, the 6 and 9 days of overload resulted in 37.0±12.81 and 44.8±12.66% hypertrophy, respectively (FIG. 2A). At both 6 and 9 days, S6K phosphorylation was elevated as expected. However, the finding that S6K1 acetylation was also increased following overload and increased from day 6 to 9 and the activity of SIRT1 was highest following 6 days of overload was novel.

EXAMPLE 2

Since metabolic stress inhibits mTOR and skeletal muscle hypertrophy and activates SIRT1, overload-induced skeletal muscle hypertrophy could be prevented by regulation of SIRT1 levels. Two lines of transgenic mice were used to demonstrate the inhibition of SIRT 1 and that altering SIRT1 activity effects muscle growth in vivo. In the first mouse line (SIRT mKO), the deacetylase domain of SIRT1 (exon 4) was removed using Cre-LOX technology and an MCK-Cre, resulting in a muscle-specific SIRT1 activity.

Figure 3A:
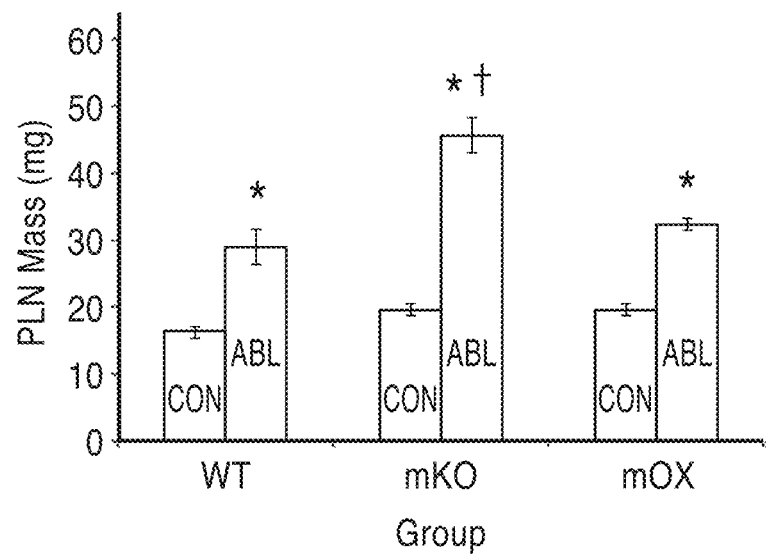
FIG. 3A is a graph comparing muscle mass where mKO mice display increased growth in response to overload and mOX mice growth was blunted compared to WT controls.
Figure 3B:
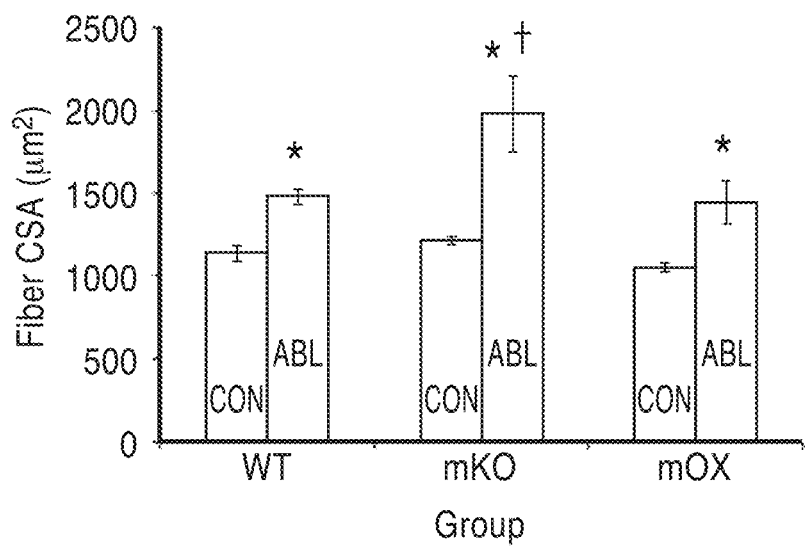
FIG. 3B is a graph comparing muscle fiber in response to overload.
Figure 4A:
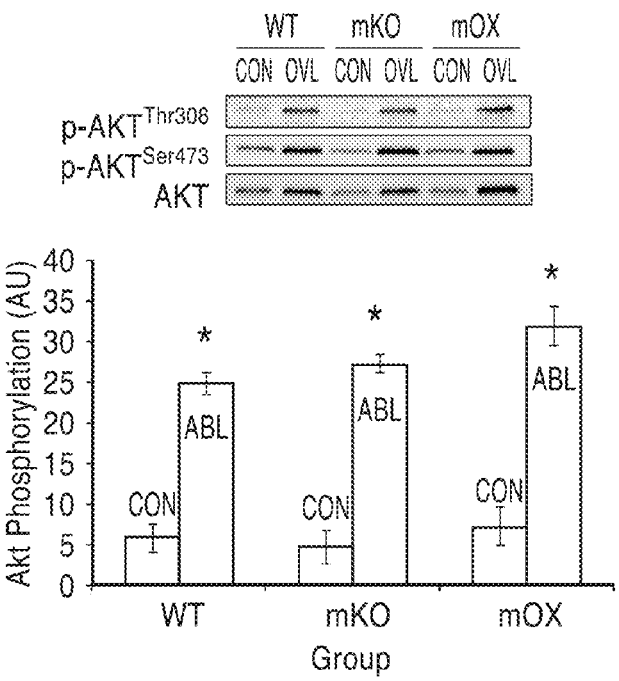
FIG. 4A is a graph of control (CON) and hypertrophied (ABL) plantaris muscles analyzed for phosphorylation of Akt.
Figure 4B:
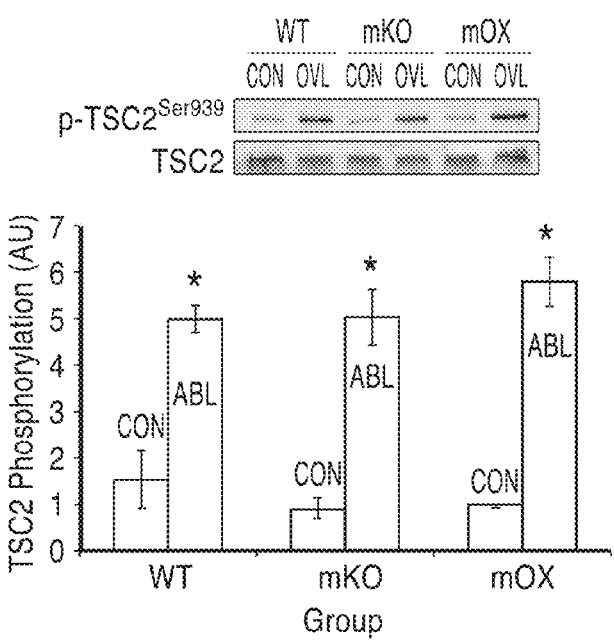
FIG. 4B is a graph of control (CON) and hypertrophied (ABL) plantaris muscles analyzed for phosphorylation of TSC2.
Figure 4C:
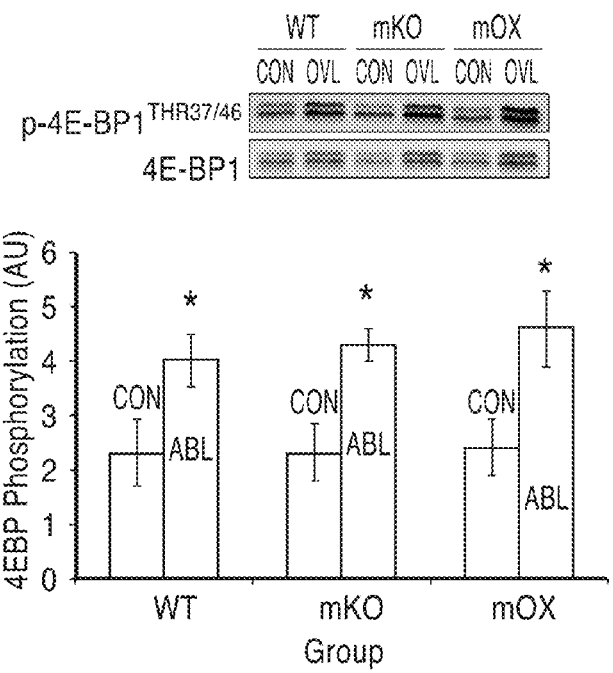
FIG. 4C is a graph of control (CON) and hypertrophied (ABL) plantaris muscles analyzed for phosphorylation of 4EBP1.
Figure 4D:
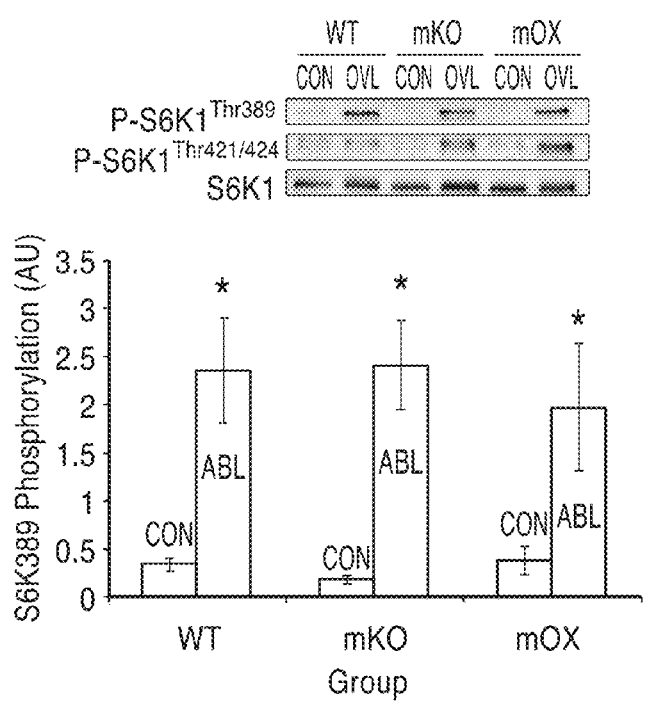
FIG. 4D is a graph of control (CON) and hypertrophied (ABL) plantaris muscles analyzed for phosphorylation of S6K1. Phosphorylation of proteins up and downstream mTOR was increased to a similar extent in WT, mKO and mOX mice.

In the second mouse line (SIRT1 mOX), the MCK-Cre-induced removal of a STOP cassette resulted in the constitutive overexpression of SIRT1. The GTN and SOL muscles of these animals were removed and the PLN muscle was overloaded for 14 days. As expected from the rat data of Example 1, removal of SIRT resulted in an 81% greater increase in skeletal muscle mass and fiber cross-sectional area as shown in FIG. 3A and FIG. 3B respectively. The mOX mice showed a small decrease in muscle mass after 14 days of overload (18% less) compared to WT controls, but no difference in fiber CSA was observed.

To determine whether SIRT1 inhibited skeletal muscle hypertrophy by impairing growth signaling, the phosphorylation of proteins upstream and downstream of the growth regulator mTOR was evaluated. Control (CON) and hypertrophied (ABL) plantaris muscles were analyzed for phosphorylation of Akt, TSC2, 4EBP1, and S6K1.

As shown in FIG. 4A through FIG. 4D, phosphorylation of proteins upstream and downstream of mTOR is increased to a similar extent in WT, mKO and mOX mice. Neither proteins upstream, Akt (FIG. 4A) or TSC2 (FIG. 4B), nor those downstream, 4EBP (FIG. 4C) or S6K (FIG. 4D) of mTOR were more activated in the SIRT1 mKO mice. Accordingly, hypertrophic signaling is not altered in SIRT mKO mice.

EXAMPLE 3

Figure 5:
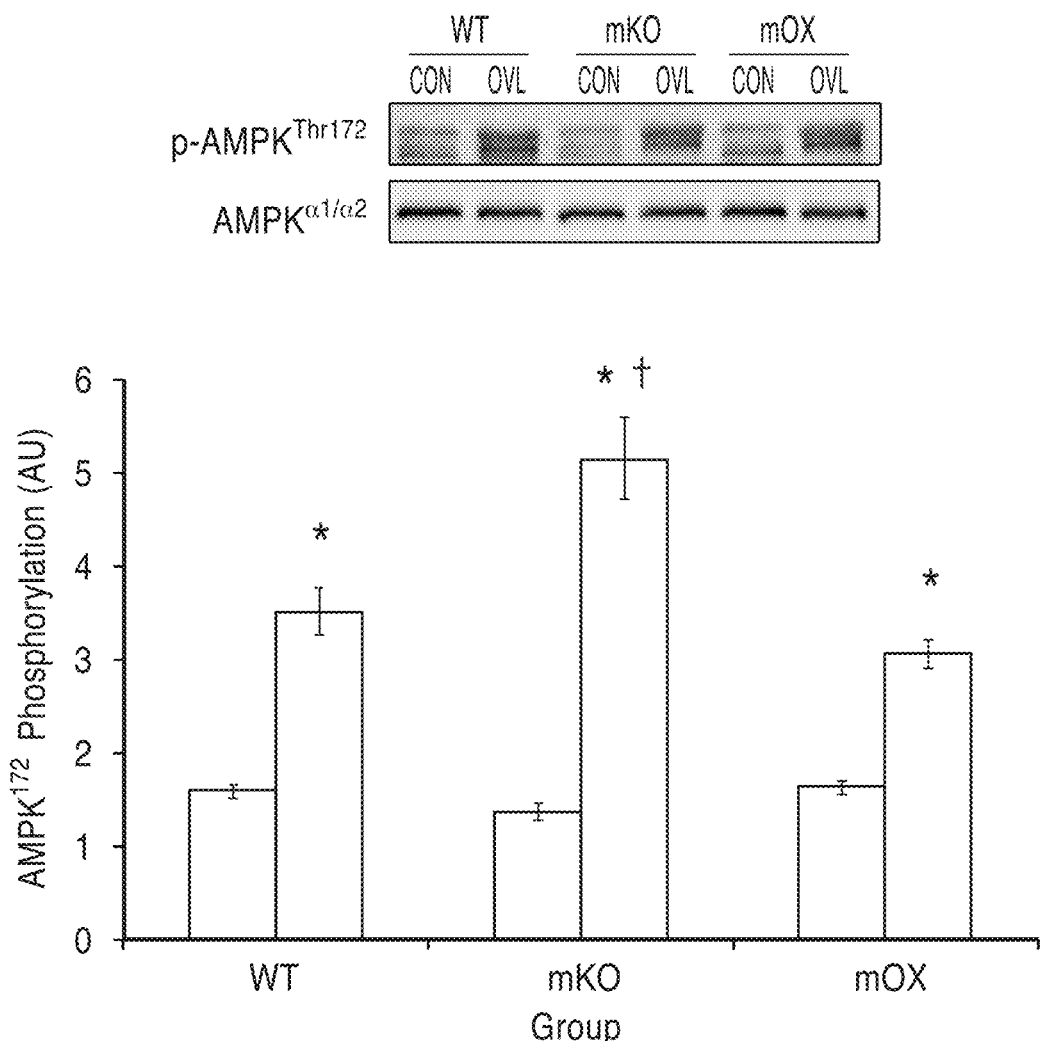
FIG. 5 is a graph of AMPK phosphorylation at Thr172 of control (CON) and hypertrophied (ABL) plantaris muscles demonstrating that phosphorylation of AMPK is increased to a greater extent in mKO mice compared to WT and mOX mice.

Since metabolic stress is known to increase AMPK activity, and $\alpha$1-AMPK is activated by overload and impairs muscle growth, activation of AMPK in the mKO mice was determined. Control (CON) and hypertrophied (ABL) plantaris muscles were analyzed for AMPK phosphorylation at Thr172. As seen in FIG. 5, phosphorylation of AMPK and its activity were higher in SIRT1 mKO mice compared to WT and mOX mice. Metabolic stress signaling through AMPK is elevated during hypertrophy in mKO mice.

Contrary to expectations, the greater rate of muscle hypertrophy in the mKO mice was not accompanied by an increase in mTOR signaling through S6K1 and 4EBP. It had been observed that skeletal muscle hypertrophy is normal in mice where S6K1 cannot be activated. However, increased muscle growth without increased mTOR signaling in general is rare.

In addition, AMPK activity is known to limit load-induced skeletal muscle hypertrophy, and was higher in the mKO mice than in either the WT or the mOX mice. SIRT1 and AMPK signaling are also interdependent, meaning that proper activation of AMPK requires SIRT1. Therefore, the data suggests that the AMPK limits load-induced skeletal muscle growth through the activation of SIRT1. During overload, $\alpha$1-AMPK is activated, which then turns on SIRT1 and slows muscle growth. In the absence of SIRT1, AMPK is unable to slow muscle growth and the accelerated rate of muscle growth results in greater activation of AMPK.

EXAMPLE 4

Figure 6:
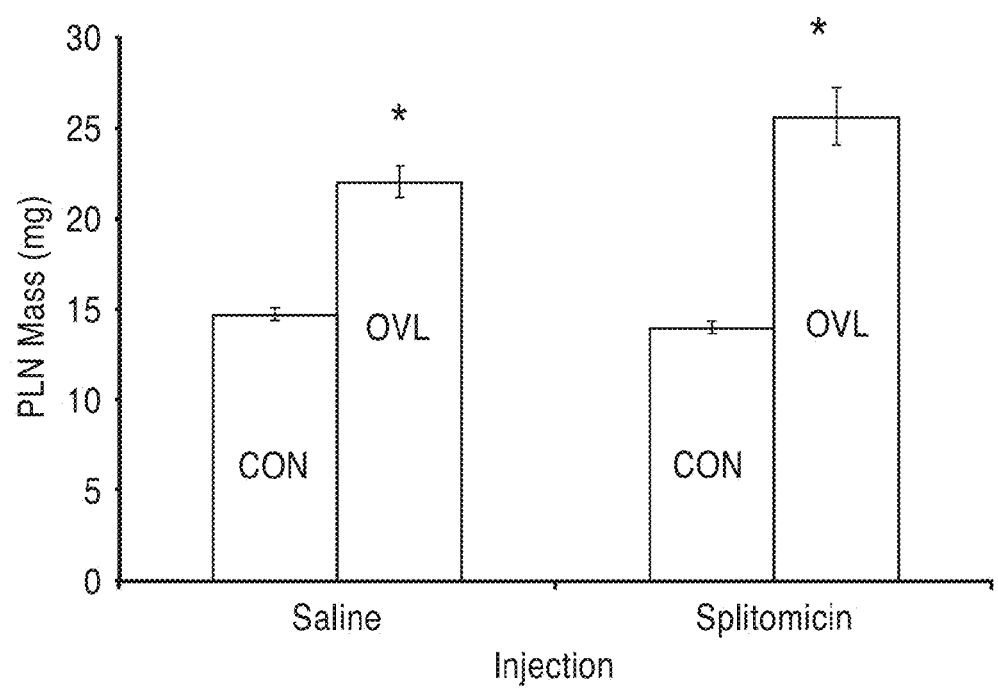
FIG. 6 is a graph of 14 days of overload performed in wild type mice concurrent with daily injection of either saline (CON) or Splitomycin (Split) demonstrating that pharmacological inhibition of SIRT1 increases muscle hypertrophy.

To determine whether the effect of SIRT1 on overload-induced muscle hypertrophy required genetic ablation or whether pharmacological ablation of SIRT1 activity could mimic the effect of the knockout, GTN and SOL muscles of wild type mice were removed and half of the mice received daily injections of the SIRT1 inhibitor Splitomycin. There were 14 days of overload performed in wild type mice concurrent with daily injection of either saline (CON) or Splitomycin (Split). Following the 14 days of treatment, those animals receiving daily Splitomycin injections showed 65% more hypertrophy than mice injected with saline as seen in FIG. 6. This demonstrated that administration of pharmacological SIRT1 inhibitors increases muscle hypertrophy in genetically normal mice.

Accordingly, it was shown that SIRT1 functionally inhibits load-induced skeletal muscle in an mTOR activity-independent manner. This suggests that SIRT1 is co-regulating a process that limits the rate of muscle protein synthesis in response to load. Interestingly, even though SIRT1 had a dramatic effect on muscle mass and CSA in the overload group, knocking out or overexpressing SIRT1 in skeletal muscle has no effect on basal muscle mass. This indicates that developmental muscle growth may not be limited by SIRT1. Instead it seems that only adaptive growth in response to loading is affected by SIRT1. This may partially underlie the concurrent training effect, where concurrent strength and high intensity endurance exercise (known to activate SIRT1) results in less hypertrophy than strength training alone. The fact that injection of a pharmacological inhibitor of SIRT1 can replicate the effect of SIRT1 knockout suggests that this strategy should be effective in increasing the effect of resistance exercise on muscle mass.

From the discussion above it will be appreciated that the invention can be embodied in various ways, including the following:

1. A method for increasing skeletal muscle growth in mammals, comprising: inhibiting the activity of sirtuins in skeletal muscles; and loading the skeletal muscles that have inhibited sirtuin activity.

2. A method as recited in any previous embodiment, further comprising: increasing calorie intake of the mammal while sirtuin activity is inhibited in the skeletal muscles.

3. A method as recited in any previous embodiment, further comprising: loading the skeletal muscles of the mammal without aerobic activity; wherein natural stimulation of sirtuin activity is avoided.

4. A method as recited in any previous embodiment, further comprising: administering muscle growth promoting amino acids to the skeletal muscles during a treatment period.

5. A method as recited in any previous embodiment, wherein the sirtuin activity comprises SIRT1 activity.

6. A method as recited in any previous embodiment, wherein the SIRT1 inhibitor comprises splitomycin, Suramin Sodium, Salermide, EX 527, Tenovin-6, SIRT1 Inhibitor IV-(S)-35, SIRT1/2 Inhibitor IV-Cambinol, SIRT2 Inhibitor-AGK2, Sirtinol and Tenovin-1 alone or in combination.

7. A method as recited in any previous embodiment, further comprising: delivering a therapeutic dose of a SIRT1 inhibitor to skeletal muscles of a mammal; wherein the therapeutic dose of SIRT1 inhibitor comprises delivering multiple bolus volumes of the inhibitor with a frequency over a duration that comprises a period of time for treatment; and wherein SIRT1 inhibition is achieved during the period of time.

8. A method as recited in any previous embodiment, wherein the therapeutic dose comprises between about 0.025 mg to about 50 mg per kilogram mammal body weight of the SIRT1 inhibitor.

9. A method as recited in any previous embodiment, wherein the period of time for treatment comprises more than one day.

10. A method as recited in any previous embodiment, wherein the period of time for treatment comprises at least a two week period; and wherein the therapeutic dose comprises between about 0.025 mg to about 50 mg/kg body weight being delivered per day over the time for treatment.

11. A method as recited in any previous embodiment, wherein the delivery of the therapeutic dose is performed by intramuscular injection in the body of the mammal.

12. A method of any previous embodiment, wherein the bolus volumes are delivered by oral or systemic delivery.

13. A method for increasing skeletal muscle growth in mammals, comprising: inhibiting the activity of SIRT1 in skeletal muscles with an inhibitor in a mammal; suppressing natural stimulation of SIRT1 production in the mammal; and loading the skeletal muscles that have inhibited SIRT1 activity.

14. A method as recited in any previous embodiment, further comprising: administering at least one muscle growth promoting agent to the skeletal muscles during a treatment period.

15. A method as recited in any previous embodiment, wherein the growth promoting agent comprises at least one amino acid.

16. A method as recited in any previous embodiment, wherein the suppression of natural stimulation of SIRT1 production comprises: increasing calorie intake of the mammal; and loading the skeletal muscles of the mammal without aerobic activity; wherein natural stimulation of SIRT1 production is suppressed.

17. A method as recited in any previous embodiment, wherein the SIRT1 inhibitor comprises splitomycin.

18. A method for increasing skeletal muscle growth in mammals, comprising: inhibiting the activity of SIRT1 in skeletal muscles with an inhibitor in a mammal; suppressing natural stimulation of SIRT1 production in the mammal; administering at least one muscle growth promoting agent to the skeletal muscles during a treatment period; and loading the skeletal muscles with inhibited SIRT1 activity.

19. A method as recited in any previous embodiment, wherein the SIRT1 inhibitor comprises Splitomycin of a therapeutic dose of 25 mg/kg body weight.

20. A method as recited in any previous embodiment: wherein the treatment period comprises at least a two week period; and wherein the wherein the SIRT1 inhibitor comprises a dose of between 0.25 mg to 50 mg/kg body weight being delivered per day over the treatment period.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method for increasing skeletal muscle growth in mammals, comprising:
inhibiting the activity of sirtuins in skeletal muscles of a mammal; and
loading the skeletal muscles that have inhibited sirtuin activity,
wherein muscle growth of the loaded skeletal muscles is increased, wherein said sirtuin activity comprises SIRT1 activity and wherein the SIRT1 inhibitor comprises Splitomycin.

2. The method as recited in claim 1, further comprising: increasing calorie intake of the mammal while sirtuin activity is inhibited in the skeletal muscles.

3. The method as recited in claim 2, further comprising: loading the skeletal muscles of the mammal without aerobic activity;
wherein natural stimulation of sirtuin activity is avoided.

4. The method as recited in claim 1, further comprising: administering muscle growth promoting amino acids to the skeletal muscles during a treatment period.

5. The method as recited in claim 1, further comprising: delivering a therapeutic dose of a SIRT1 inhibitor to skeletal muscles of a mammal;
wherein the therapeutic dose of SIRT1 inhibitor comprises delivering multiple bolus volumes of the inhibitor with a frequency over a duration that comprises a period of time for treatment; and
wherein SIRT1 inhibition is achieved during the period of time.

6. The method as recited in claim 5, wherein the therapeutic dose comprises between about 0.025 mg to about 50 mg per kilogram mammal body weight of the SIRT1 inhibitor.

7. The method as recited in claim 5, wherein the period of time for treatment comprises more than one day.

8. The method as recited in claim 5:
wherein the period of time for treatment comprises at least a two week period; and
wherein the therapeutic dose comprises between 0.025 mg to 50 mg per kg body weight being delivered per day over the time for treatment.

9. The method of claim 5, wherein the delivery of said therapeutic dose is performed by intramuscular injection in the body of the mammal.

10. The method of claim 5, wherein the bolus volumes are delivered by oral or systemic delivery.

11. A method for increasing skeletal muscle growth in mammals, comprising:
inhibiting the activity of SIRT1 in skeletal muscles of a mammal with an inhibitor;
suppressing natural stimulation of SIRT1 production in the mammal; and
loading the skeletal muscles that have inhibited SIRT1 activity,
wherein muscle growth of the loaded skeletal muscles is increased, wherein the SIRT1 inhibitor comprises Splitomycin.

12. The method as recited in claim 11, further comprising: administering at least one muscle growth promoting agent to the skeletal muscles during a treatment period.

13. The method as recited in claim 12, wherein said growth promoting agent comprises at least one amino acid.

14. The method as recited in claim 11, wherein said suppression of natural stimulation of SIRT1 production comprises:
increasing calorie intake of the mammal; and
loading the skeletal muscles of the mammal without aerobic activity;
wherein natural stimulation of SIRT1 production is suppressed.

15. A method for increasing skeletal muscle growth in mammals, comprising:
   inhibiting the activity of SIRT1 in skeletal muscles with an inhibitor in a mammal;
   suppressing natural stimulation of SIRT1 production in the mammal;
   administering at least one muscle growth promoting agent to the skeletal muscles during a treatment period; and
   loading the skeletal muscles with inhibited SIRT1 activity, wherein the SIRT1 inhibitor comprises Splitomycin.

16. The method as recited in claim 15, wherein the SIRT1 inhibitor comprises Splitomycin of a therapeutic dose of 25 mg per kg body weight.

17. The method as recited in claim 15:
   wherein the treatment period comprises at least a two week period; and
   wherein the SIRT1 inhibitor comprises a dose of between 0.25 mg to 50 mg per kg body weight being delivered per day over the treatment period.

* * * * *